(12) United States Patent
Katakowski et al.

(10) Patent No.: US 11,660,271 B2
(45) Date of Patent: May 30, 2023

(54) SYSTEM AND METHOD FOR ISOLATING EXTRACELLULAR VESICLES

(71) Applicant: FOREVER LABS, INC., Ann Arbor, MI (US)

(72) Inventors: Mark Katakowski, Ann Arbor, MI (US); Ann Hozeska-Solgot, West Bloomfield, MI (US)

(73) Assignee: FOREVER LABS, INC., Ann Arbor, MI (US)

( * ) Notice: Subject to any disclaimer, the term of this patent is extended or adjusted under 35 U.S.C. 154(b) by 336 days.

(21) Appl. No.: 16/259,648

(22) Filed: Jan. 28, 2019

(65) Prior Publication Data
US 2019/0231692 A1    Aug. 1, 2019

Related U.S. Application Data (60) Provisional application No. 62/695,590, filed on Jul. 9, 2018, provisional application No. 62/623,062, filed on Jan. 29, 2018.

(51) Int. Cl.

| | | |
|---|---|---|
| *C12N 5/078* | (2010.01) | |
| *C12N 5/077* | (2010.01) | |
| *G01N 33/50* | (2006.01) | |
| *A61K 9/16* | (2006.01) | |
| *A61M 1/02* | (2006.01) | |
| *A61M 1/38* | (2006.01) | |
| *A61M 1/36* | (2006.01) | |
| *C12N 5/0775* | (2010.01) | |
| *A61K 9/00* | (2006.01) | |
| *A61K 35/16* | (2015.01) | |
| *A61K 35/19* | (2015.01) | |
| *A61K 35/28* | (2015.01) | |
| *A61M 5/31* | (2006.01) | |
| *B01D 21/26* | (2006.01) | |

(52) U.S. Cl.
CPC .......... *A61K 9/1682* (2013.01); *A61K 9/0019* (2013.01); *A61K 9/1652* (2013.01); *A61K 35/16* (2013.01); *A61K 35/19* (2013.01); *A61K 35/28* (2013.01); *A61M 1/029* (2013.01); *A61M 1/0272* (2013.01); *A61M 1/3693* (2013.01); *A61M 1/38* (2013.01); *A61M 5/31* (2013.01); *B01D 21/262* (2013.01); *C12N 5/0644* (2013.01); *C12N 5/0663* (2013.01); *C12N 5/0669* (2013.01); *G01N 33/5002* (2013.01); *A61M 2005/3114* (2013.01); *A61M 2202/0415* (2013.01); *A61M 2202/0427* (2013.01); *A61M 2202/10* (2013.01)

(58) Field of Classification Search
CPC . C12N 5/0669; C12N 5/0644; G01N 33/5002
See application file for complete search history.

(56) References Cited

U.S. PATENT DOCUMENTS

| | | |
|---|---|---|
| 6,835,353 B2 | 12/2004 | Smith et al. |
| 10,351,813 B2 | 7/2019 | Johnson et al. |
| 11,129,930 B2 | 9/2021 | Esteron |
| 2002/0185457 A1 | 12/2002 | Smith et al. |
| 2007/0208321 A1 | 9/2007 | Leach et al. |
| 2010/0125236 A1 | 5/2010 | Bare et al. |
| 2012/0015796 A1 | 1/2012 | Leach et al. |
| 2012/0053041 A1 | 3/2012 | Ihm et al. |
| 2015/0023939 A1 | 1/2015 | Woodell-May |
| 2016/0160173 A1 | 6/2016 | Johnson et al. |
| 2017/0056891 A1 | 3/2017 | Ostafin et al. |
| 2018/0164197 A1* | 6/2018 | Park ................... B01D 17/0217 |
| 2020/0009304 A1 | 1/2020 | Dorian et al. |
| 2020/0009312 A1 | 1/2020 | Min et al. |
| 2020/0009553 A1 | 1/2020 | Roth |
| 2020/0171485 A1 | 6/2020 | Heinrich |
| 2020/0179827 A1 | 6/2020 | Deregibus et al. |
| 2020/0215243 A1 | 7/2020 | Dorian et al. |
| 2021/0236428 A1 | 8/2021 | Katakowski et al. |

FOREIGN PATENT DOCUMENTS

| | | |
|---|---|---|
| EP | 2343132 B1 | 9/2017 |
| EP | 3230433 B1 | 8/2021 |
| JP | 2016-518109 A | 6/2016 |
| WO | WO-2014/159662 A1 | 10/2014 |
| WO | WO-2016/159520 A1 | 10/2016 |

OTHER PUBLICATIONS

Shin et al., High-yield isolation of extracellular vesicles using aqueous two-phase system. Scientific Reports, vol. 5 (2013) 13103. (Year: 2013).*
International Preliminary Report on Patentability, corresponding International application No. PCT/US2019/015355, dated Aug. 4, 2020.
Cosenza et al., Mesenchymal stem cells derived exosomes and microparticles protect cartilage and bone from degradation in osteoarthritis, Sci. Rep., 7(1):16214 (Nov. 2017).
Giebel et al., Clinical potential of mesenchymal stem/stromal cell-derived extracellular vesicles, Stem Cell Investig., 4:84 (Oct. 2017).
(Continued)

*Primary Examiner* — Kara D Johnson
(74) *Attorney, Agent, or Firm* — Marshall, Gerstein & Borun LLP (57) ABSTRACT

A system and method of isolating extracellular vesicles. The method includes loading one or more of blood or bone marrow into an input port of a concentration system and centrifuging one or more of the blood or bone marrow to separate one or more of red blood cells, platelet poor plasma, or platelet rich plasma/bone marrow concentrate fractions via a centrifuge device. The method further includes pumping one or more of bone marrow/platelet rich plasma fractions and platelet poor plasma fractions into a receptacle of the concentration system and adding a concentrated aqueous two-phase solution to one or more of the bone marrow concentrate/platelet rich plasma fractions and platelet poor plasma fractions. The method also includes drawing the concentrated aqueous two-phase solution and one or more of the bone marrow concentrate/platelet rich plasma fractions or platelet poor plasma fractions back into the centrifuge device to isolate one or more of extracellular vesicles and platelet rich plasma/bone marrow concentrate fractions.

22 Claims, 9 Drawing Sheets

(56) References Cited

OTHER PUBLICATIONS

Hao et al., Stem cell-derived exosomes: A promising strategy for fracture healing, Cell Prolif., 50(5):e12359 (Oct. 2017).
Huang et al., Bone marrow mesenchymal stem cell?derived extracellular vesicles improve the survival of transplanted fat grafts, Mol. Med. Rep., 16(3):3069-78 (Sep. 2017).
International Application No. PCT/US2019/015355, International Search Report and Written Opinion, dated Apr. 24, 2019.
Katakowski et al., Exosomes as Tools to Suppress Primary Brain Tumor, Cell Mol. Neurobiol., 36(3):343-52 (Apr. 2016).
Kim et al., Exosomes derived from human umbilical cord blood mesenchymal stem cells stimulates rejuvenation of human skin, Biochem. Biophys. Res. Commun., 493(2):1102-8 (Nov. 2017).
Murphy et al., Emerging role of extracellular vesicles in musculoskeletal diseases, Mol. Aspects Med., 60:123-8 (Apr. 2018).
Newton et al., Stem cell-derived exosomes: a novel vector for tissue repair and diabetic therapy, J. Mol. Endocrinol., 59(4):R155-R165 (Nov. 2017).
Rilla et al., Extracellular vesicles are integral and functional components of the extracellular matrix, Matrix Biol., 75-76:201-19 (Jan. 2019).
Shin et al., High-yield isolation of extracellular vesicles using aqueous two-phase system, Scientific Reports, 5, Article No. 13103 (Aug. 14, 2015).
Zhang et al., Exosomes Derived from Mesenchymal Stromal Cells Promote Axonal Growth of Cortical Neurons, Mol. Neurobiol., 54(4):2659-73 (May 2017).
Office Action, Canadian Patent Application No. 3,089,825, dated Oct. 20, 2020.
Kim et al., Isolation of High-Purity Extracellular Vesicles by Extracting Proteins Using Aqueous Two-Phase System, PLoS One, 10(6):e0129760 (June 2015).
Australian Patent Application No. 2019212824, Examination Report No. 1, dated May 4, 2022.
Office Action issued in Japanese Patent Application No. 2020-542124 dated Nov. 9, 2021.
European Patent Application No. 19708185.4, Communication Pursuant to Article 94(3) EPC, dated May 17, 2022.
Japanese Patent Application No. 2020-542124, Decision of Rejection, dated Jul. 5, 2022.

* cited by examiner

SYSTEM AND METHOD FOR ISOLATING EXTRACELLULAR VESICLES

TECHNICAL FIELD

This disclosure relates to cell isolation methods and devices and, in particular, to a system and method for isolating extracellular vesicles from bone marrow or blood.

BACKGROUND

Extracellular vesicles (such as exosomes) are released by cells that efficiently transfer their molecular cargo to other cells. The therapeutic effects of extracellular vesicles derive from their cargo (such as miRNAs and proteins) and surface molecules. In addition, extracellular vesicles can be functional components of the extracellular matrix that participate in organization, cell-regulation, and determining the physical properties of connective tissues and bone.

Injections of platelet rich plasma (PRP) and bone marrow concentrate (BMC) are used in clinical applications to promote healing, stimulate tissue regrowth, ameliorate inflammation, and rejuvenate uninjured endogenous tissue. Extracellular vesicles are found in all biofluids, including the blood and marrow, and have been demonstrated to confer many of the effects of the cells that they are produced by. For example, extracellular vesicles from umbilical cord or bone marrow mesenchymal stem cells (MSCs) have been demonstrated to stimulate rejuvenation of human skin, or improve the survival of transplanted fat grafts. It has been demonstrated that extracellular vesicles from bone MSCs exerted similar chondroprotective and anti-inflammatory function and protected mice from developing osteoarthritis, suggesting that extracellular vesicles reproduce the main therapeutic effect of the MSCs. Indeed, recent scientific and clinical evidence suggests that MSCs may not primarily exert their therapeutic functions in a cellular, but rather in a paracrine manner; extracellular vesicles (such as exosomes and microvesicles) have been identified as major mediators of these paracrine effects.

Due to their low density and small size, extracellular vesicles are commonly isolated by filtration, ultra-centrifugation, immunoaffinity, microfluidics, or polymeric precipitation. Current devices employed to partition blood or bone marrow (into fractions such as red blood cells (RBCs), platelet poor plasma (PPP), and BMC or PRP) use low-speed centrifugation, and extracellular vesicles are not effectively isolated or concentrated into one partition. Thus, devices that concentrate whole blood or bone marrow are not concentrating the biological agents, such as extracellular vesicles that are likely to be delivering a substantial portion of the therapeutic effect.

SUMMARY OF THE DISCLOSURE

In accordance with one exemplary aspect of the present disclosure, a method of isolating extracellular vesicles comprises loading one or more of blood or bone marrow into an input port of a concentration system, and centrifuging one or more of the blood or bone marrow to separate one or more of red blood cells, platelet poor plasma, or platelet rich plasma/bone marrow concentrate fractions via a centrifuge device of the concentration system. The method further includes pumping one or more of bone marrow/platelet rich plasma fractions and platelet poor plasma fractions into a first receptacle of the concentration system, and adding a concentrated aqueous two-phase solution, such as a poly (ethylene glycol)-dextran (PEG-DEX) solution, to one or more of the bone marrow concentrate/platelet rich plasma fractions and platelet poor plasma fractions. The method further includes drawing the concentrated aqueous two-phase solution and one or more of the bone marrow concentrate/platelet rich plasma fractions or platelet poor plasma fractions back into the centrifuge device to isolate one or more of extracellular vesicles and platelet rich plasma/bone marrow concentrate fractions. The method also includes pumping one or more of the bone marrow concentrate/platelet rich plasma fractions and isolated extracellular vesicles into a syringe for injection.

According to another aspect of the present disclosure, a method of isolating extracellular vesicles comprises disposing a concentrated aqueous two-phase PEG-DEX solution in a syringe or a receptacle and adding one or more of platelet poor plasma fractions or bone marrow/platelet rich plasma fractions into the concentrated aqueous two-phase solution. The method further includes centrifuging the concentrated aqueous two-phase solution and one or more of the platelet poor plasma fractions or the bone marrow/platelet rich plasma fractions disposed in the syringe or the receptacle to isolate one or more of extracellular vesicles and bone marrow/platelet rich plasma fractions. The method also includes creating a pellet including one or more of extracellular vesicles and bone marrow/platelet rich plasma fractions from centrifuging of the aqueous two-phase solution and one or more of the platelet poor plasma fractions and the bone marrow/platelet rich plasma fractions, the pellet for injection.

According to yet another example of the present disclosure, a system for isolating extracellular vesicles comprises a first input port for receiving one or more of blood or bone marrow, and a centrifuge device coupled to the input port for separating fractions of one or more of red blood cells, platelet poor plasma, and/or bone marrow concentrate/platelet rich plasma. The system further includes a receptacle for collecting one or more of bone marrow concentrate fractions/platelet rich plasma fractions or platelet poor plasma fractions centrifuged from the centrifuge device, the receptacle coupled to the centrifuge device, and a second inlet port coupled to the first receptacle and for receiving an aqueous two-phase solution via a syringe coupled to the second inlet port. An outlet port is coupled to the centrifuge device for receiving extracellular vesicles isolated in the centrifuge device. So configured, after the centrifuge device separates one or more of the blood and the bone marrow into one or more of red blood cells, platelet poor plasma, and/or bone marrow concentrate/platelet rich plasma fractions, the aqueous two-phase solution is added to the first receptacle having one or more of the bone marrow concentrate/platelet rich plasma fractions or platelet poor plasma fractions disposed therein. The aqueous two-phase solution and the one or more of the bone marrow concentrate fractions/platelet rich plasma fractions or platelet poor plasma fractions are then drawn back into the centrifuge device to isolate one or more of extracellular vesicles or the bone marrow concentrate/platelet rich plasma fractions for injection.

In further accordance with any one or more of the exemplary aspects, the system for isolating extracellular vesicles or any method of the present disclosure may include any one or more of the following preferred forms.

In some aspects, the method further comprises premixing the aqueous two-phase solution at a predetermined concentration before adding the concentrated aqueous two-phase solution to one or more of the bone marrow concentrate/ platelet rich plasma fractions and platelet poor plasma fractions. In addition, the method may comprise allowing a period of time for room temperature incubation after adding the concentrated aqueous two-phase solution to one or more of the bone marrow concentrate/platelet rich plasma fractions and platelet poor plasma fractions. In addition, the method may comprise pumping the solution and extracellular vesicles-poor plasma into the first receptacle after drawing the concentrated aqueous two-phase solution and one or more of the bone marrow concentrate/platelet rich plasma fractions or platelet poor plasma fractions back into the centrifuge device for centrifugation.

According to other aspects, drawing the concentrated aqueous two-phase solution and one or more of the bone marrow concentrate/platelet rich plasma fractions or platelet poor plasma fractions back into the centrifuge device for centrifugation may comprise isolating extracellular vesicles from the platelet poor plasma fractions, creating an extracellular vesicles pellet for injection. In addition, adding a concentrated aqueous two-phase solution to one or more of the bone marrow concentrate/platelet rich plasma fractions and platelet poor plasma fractions may comprise adding the concentrated aqueous two-phase solution to one or more of the bone marrow concentrate/platelet rich plasma fractions and platelet poor plasma fractions based upon a volume of one or more of the bone marrow concentrate/platelet rich plasma fractions and platelet poor plasma fractions in the first receptacle.

In still other aspects, pumping one or more of bone marrow/platelet rich plasma fractions and platelet poor plasma fractions into a first receptacle of the concentration system may comprise pumping only the platelet poor plasma fractions into the first receptacle and then pumping the bone marrow/platelet rich plasma fractions into a syringe. In this example, adding a concentrated aqueous two-phase solution to one or more of bone marrow concentrate/platelet rich plasma fractions and platelet poor plasma fractions may comprise adding a concentrated aqueous two-phase solution to only the platelet poor plasma fractions. In addition, drawing the concentrated aqueous two-phase solution and one or more of the bone marrow concentrate/platelet rich plasma fractions or platelet poor plasma fractions back into the centrifuge device for centrifugation may comprise drawing the concentrated aqueous two-phase solution and the platelet poor plasma fractions back into the centrifuge device for centrifugation. Further, pumping one or more of the bone marrow concentrate/platelet rich plasma fractions and extracellular vesicles into a syringe for injection may comprise pumping the extracellular vesicles into the syringe for injection.

In still yet other aspects, the method may further comprise determining a volume of aqueous two-phase solution to be injected based upon the volume of the bone marrow/platelet rich plasma fractions isolated in the syringe, reducing the concentration of aqueous two-phase solution used and minimizing the effect of the aqueous two-phase solution on nucleated cells in the bone marrow/platelet rich plasma fractions. In addition, the method may include determining a volume of the extracellular vesicles based on the volume of the bone marrow/platelet rich plasma fractions isolated in the syringe.

In other aspects, the method may comprise premixing the aqueous two-phase solution at a predetermined concentration before disposing in the syringe or the receptacle. In addition, adding one or more of platelet poor plasma fractions or bone marrow/platelet rich plasma fractions into the concentrated aqueous two-phase solution may comprise adding an amount of platelet poor plasma such that the amount of the concentrated aqueous two-phase solution is diluted, such as diluted to a working solution of about 1.5% concentrated aqueous two-phase solution in one example. Further, the method may comprise mixing the extracellular vesicle created with biofluid including one or more of platelet rich plasma, bone marrow concentrate or platelet poor plasma.

In still yet other aspects, the system may include a syringe coupled to the second inlet port and, thus, the first receptacle, the syringe including a pre-mixed aqueous two-phase solution to be added to one or more of the bone marrow concentrate fractions/platelet rich plasma fractions or platelet poor plasma fractions disposed within the first receptacle. In addition, an amount of the aqueous solution added to the bone marrow concentrate/platelet rich plasma fractions or platelet poor plasma fractions may be based upon an output volume of one or more of the bone marrow concentrate/platelet rich plasma fractions or platelet poor plasma fractions disposed in the receptacle. The system may further comprise an isolation syringe to be coupled to the outlet port for receiving one or more of the extracellular vesicles isolated or the bone marrow concentrate fractions/platelet rich plasma fractions created after centrifugation in the centrifuge device. Further, the receptacle may include a first receptacle, and the system may further comprise a second receptacle for collecting red blood cell fractions centrifuged from the centrifuge device, the second receptacle coupled to the centrifuge device.

Additional optional aspects and features are disclosed, which may be arranged in any functionally appropriate manner, either alone or in any functionally viable combination, consistent with the teachings of the disclosure. Other aspects and advantages will become apparent upon consideration of the following detailed description.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings are necessarily to scale.

DETAILED DESCRIPTION

Generally, a system and methods of isolating extracellular vesicles are disclosed. The system includes a first input port for receiving one or more of blood or bone marrow, and a centrifuge device is coupled to the input port for separating fractions of one or more of red blood cells, platelet poor plasma, and/or bone marrow concentrate/platelet rich plasma. The system also includes a first receptacle for collecting one or more of bone marrow concentrate fractions/platelet rich plasma fractions or platelet poor plasma fractions centrifuged from the centrifuge device, and the first receptacle is coupled to the centrifuge device. A second receptacle for collecting red blood cell fractions centrifuged from the centrifuge device is also included, and the second receptacle is likewise coupled to the centrifuge device. A second inlet port is coupled to the first receptacle and receives a concentrated aqueous two-phase solution, such as a poly(ethylene glycol)-dextran (PEG-DEX) solution, via a syringe coupled to the second inlet port, and an outlet port is coupled to the centrifuge device for receiving extracellular vesicles isolated in the centrifuge device. So configured, after the centrifuge device separates one or more of the blood and the bone marrow into one or more of red blood cells, platelet poor plasma, and/or bone marrow concentrate/platelet rich plasma fractions, the concentrated aqueous two-phase solution is added to the first receptacle having one or more of the bone marrow concentrate/platelet rich plasma fractions or platelet poor plasma fractions disposed therein. The concentrated aqueous two-phase solution and the one or more of the bone marrow concentrate fractions/platelet rich plasma fractions or platelet poor plasma fractions are then drawn back into the centrifuge device to isolate one or more of extracellular vesicles or the bone marrow concentrate/platelet rich plasma fractions for injection.

More specifically, using an aqueous two-phase solution, the extracellular vesicles can be isolated from platelet poor plasma in a centrifugation process, such as a 10-minute centrifugation process. The platelet poor plasma can be from peripheral blood or from bone marrow. The isolated extracellular vesicles can then be applied directly, or suspended within platelet rich plasma or bone marrow concentrate and then applied. This isolation protocol may be used in conjunction with platelet rich plasma/bone marrow concentrate systems, significantly extending the therapeutic potential of these biological treatments.

Figure 1:
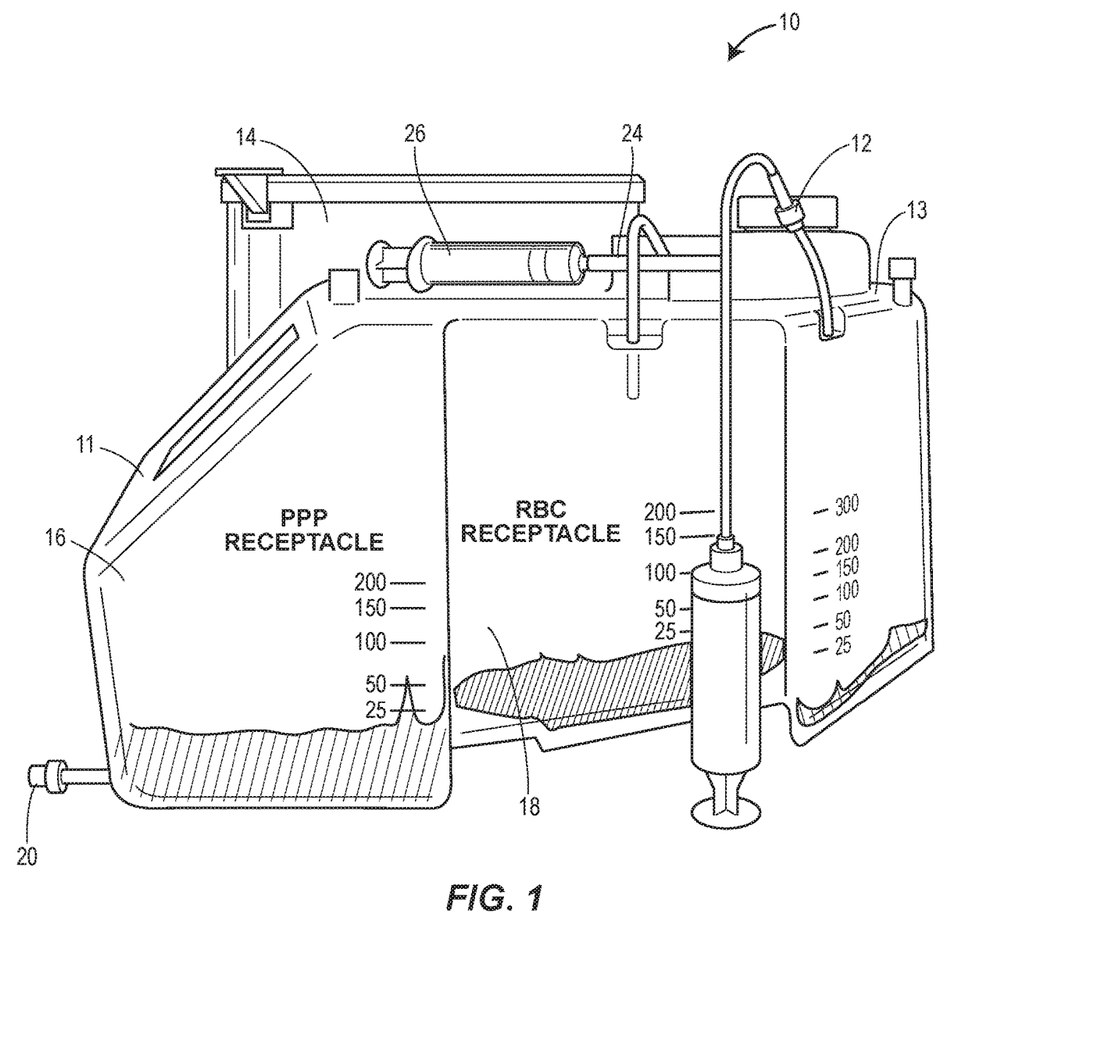
FIG. 1 is a perspective view of a system for isolating extracellular vesicles in accordance with an aspect of the present disclosure.

Referring now to FIG. 1, a system for isolating extracellular vesicles 10, such as concentration system, is depicted. The concentration system is typically used to concentrate whole blood or bone marrow. For example, the bone marrow concentrate fraction may be used for the biologic injection.

More specifically, the system 10 includes a compartment 11 and a first input port 12 for receiving one or more of blood or bone marrow that is one or more of adjacent to or disposed on a portion of the compartment 11. In one example, the first input port 12 is disposed on a first side portion 13 of the housing 11, as depicted in FIG. 1. A centrifuge device 14 is coupled to the input port 12 and disposed adjacent to a second side portion 15 (FIG. 3A) of the compartment 11. The centrifuge device 14 separates fractions of one or more of red blood cells, platelet poor plasma, and/or bone marrow concentrate/platelet rich plasma directed to the centrifuge device 14 via the first input port 12, for example. In addition, the system 10 also includes a first receptacle 16 for collecting one or more of bone marrow concentrate fractions/platelet rich plasma fractions or platelet poor plasma fractions centrifuged from the centrifuge device 14. The first receptacle 16 is coupled to the centrifuge device 14 and is disposed adjacent to the first side portion 13 of the compartment 11. Like the first receptacle 16, the second receptacle 18 is also coupled to the centrifuge device 14 and disposed adjacent to the first side portion 13 of the compartment 11. The second receptacle 18 collects red blood cell fractions centrifuged from the centrifuge device 14, for example.

Figure 2:
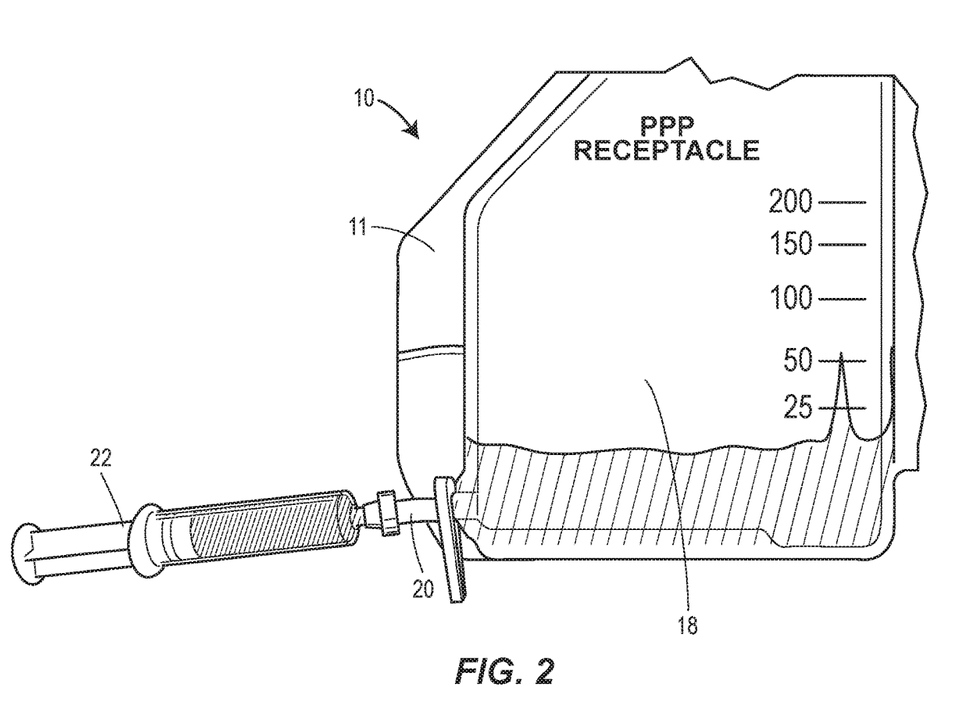
FIG. 2 is another perspective view of part of the system of FIG. 1.

A second inlet port 20 is coupled to the first receptacle 16 and receives a concentrated aqueous two-phase solution, such as a PEG-DEX solution, as explained more below. In one example, and as depicted in FIG. 2, a syringe 22 is coupled to the second inlet port 20 and includes a concentrated two-phase solution to be added to one or more of the platelet poor plasma and/or the bone marrow concentrate/platelet rich plasma fractions disposed within the first receptacle 16.

The aqueous two-phase solution includes any solution that enables separation and partitioning of microvesicles during centrifugation. More generally, aqueous (or water-based) solutions, being polar, are immiscible with non-polar organic solvents (chloroform, toluene, hexane etc.) and form a two-phase system, for example. The formation of the distinct phases is affected by the pH, temperature, and ionic strength of the two components, and separation occurs when the amount of a polymer present exceeds a certain limiting concentration, which is determined by these factors. In one example, and as noted above, the aqueous two-phase solution includes the concentrated PEG-DEX solution. In this example, an "upper phase" is formed by the more hydrophobic polyethylene glycol (PEG), which is of lower density than a "lower phase," consisting of the more hydrophilic and denser dextran solution.

Referring back to FIG. 1, an outlet port 24 is disposed on a top portion 25 (FIG. 3A) of the compartment 11 and is coupled to the centrifuge device 14. In one example, an isolation syringe 26 is coupled to the outlet port 24. The isolation syringe 26 receives one or more of the extracellular vesicles isolated at least by the centrifuge device 14 according to one of the centrifuge processes described below and/or the bone marrow concentrate fractions/platelet rich plasma fractions created after centrifugation in the centrifuge device.

So configured, upon loading one or more of blood or bone marrow into the input port 12, the centrifuge device 14 separates the blood into red blood cells and separates the bone marrow into one or more of platelet poor plasma and/or bone marrow concentrate/platelet rich plasma fractions. One or more of the platelet poor plasma or the bone marrow concentrate/platelet rich plasma fractions is pumped into the first receptacle 16 and the red blood cells are directed, such as pumped, into the second receptacle 18. As explained more below, a concentrated aqueous two-phase solution is then added to the one or more of the bone marrow concentrate/platelet rich plasma fractions and/or platelet poor plasma fractions disposed in the first receptacle 16. Thereafter, the aqueous two-phase solution and the one or more of the bone marrow concentrate fractions/platelet rich plasma fractions or platelet poor plasma fractions are drawn back into the centrifuge device 14 to isolate one or more of extracellular vesicles or the bone marrow concentrate/platelet rich plasma fractions for injection. Generally, and in one example, an amount of the aqeuous two-phase solution added to the bone marrow concentrate/platelet rich plasma fractions or platelet poor plasma fractions is based upon an output volume of one or more of the bone marrow concentrate/platelet rich plasma fractions or platelet poor plasma fractions disposed in the first receptacle 16, as also explained more below.

Figure 3A:
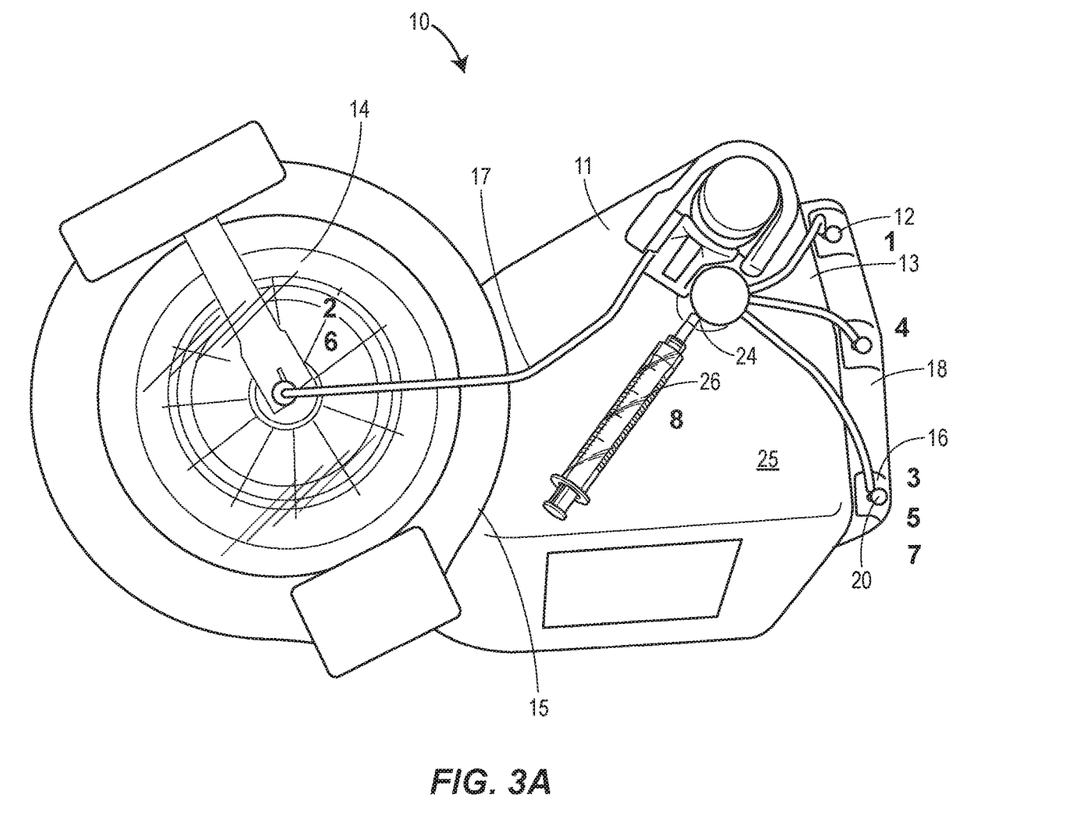
FIG. 3A is a top view of the system of FIG. 1, depicting an exemplary method of isolating vesicles in accordance with an aspect of the present disclosure.

Referring now to FIG. 3A, a top view of the system 10 of FIGS. 1 and 2 is depicted, illustrating an exemplary method 100 of isolating vesicles in accordance with one aspect of the present disclosure. More specifically, the method 100 of isolating extracellular vesicles comprises loading one or more of blood or bone marrow into the input port 12 of concentration system 10, as indicated at point 1 of FIG. 3A, for example. The method 100 next includes centrifuging one or more of the blood or bone marrow to separate one or more of red blood cells, platelet poor plasma, or platelet rich plasma/bone marrow concentrate fractions via the centrifuge device 14 of the concentration system 10, as indicated at point 2. More specifically, one or more of the blood or bone marrow is drawn from the input port 12 and into the centrifuge device 14 via tubing 17, as depicted in FIG. 3A, for example. While tubing 17 is depicted, one of ordinary skill in the art will appreciate that other mechanisms and/or processes may alternatively and/or additionally be used to direct one or more of the blood and/or bone marrow into the centrifuge device 14 and still fall within the scope of the present disclosure.

In addition, the method 100 further includes pumping one or more of the bone marrow/platelet rich plasma fractions and the platelet poor plasma fractions created after centrifugation within the centrifuge device 14 into the first receptacle 16 of the concentration system 10, as indicated at point 3 in FIG. 3A. In a similar manner, the method may further include pumping red blood cell fractions into the second receptacle 18 of the concentration system 10 as indicated at point 4, for example.

The method 100 next includes adding a concentrated aqueous two-phase solution to one or more of the bone marrow concentrate/platelet rich plasma fractions and platelet poor plasma fractions disposed within the first receptacle 16, for example, as indicated at point 5. The method further includes drawing the concentrated aqueous two-phase solution and one or more of the bone marrow concentrate/platelet rich plasma fractions or platelet poor plasma fractions back into the centrifuge device 14 to isolate one or more of extracellular vesicles and platelet rich plasma/bone marrow concentrate fractions, as indicated at point 6. In one example, the method 100 may further include pumping the aqueous two-phase solution and extracellular vesicles poor plasma (EPP) back into the first receptacle 16, as indicated at point 7, for example in FIG. 3A. The method 100 then includes pumping one or more of the bone marrow concentrate/platelet rich plasma fractions and isolated extracellular vesicles into the syringe 26 for injection, as indicated at point 8.

Figure 3B:
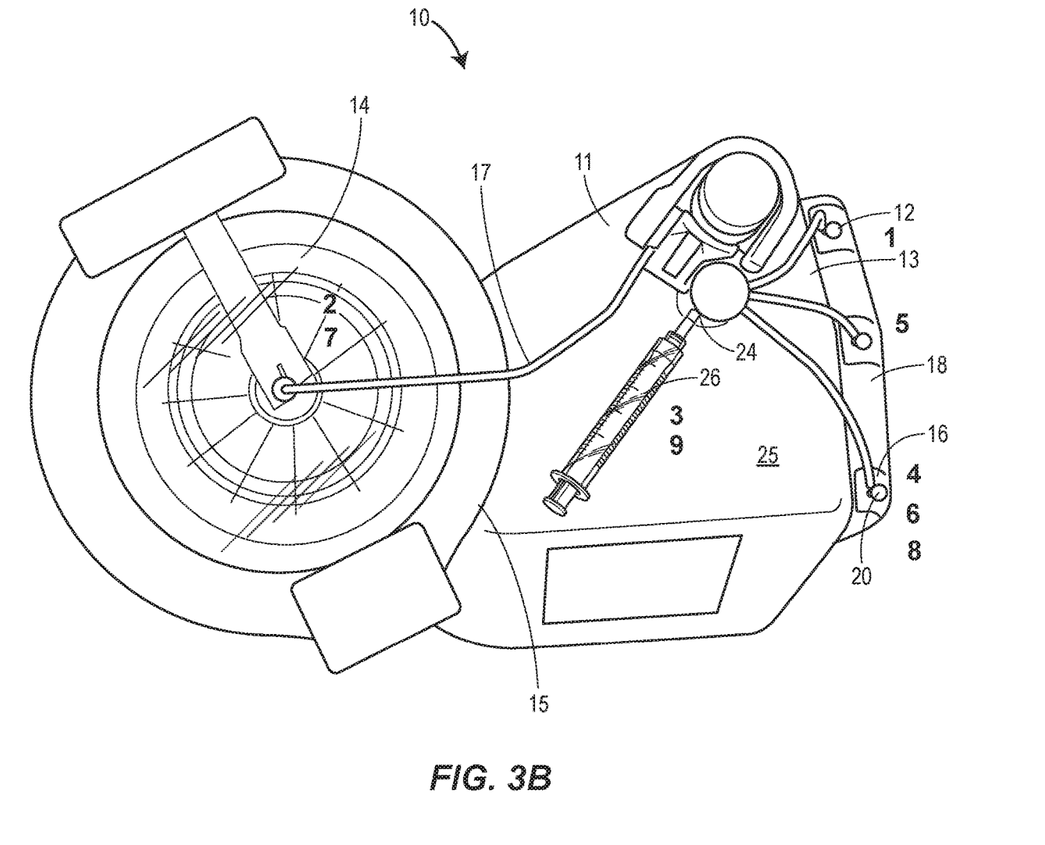
FIG. 3B is another top view of the system of FIG. 1, depicting another exemplary method of isolating vesicles in accordance with another aspect of the present disclosure.

Referring now to FIG. 3B, another top view of the system 10 of FIG. 1 is depicted, illustrating another exemplary method 200 of isolating vesicles in accordance with another aspect of the present disclosure. Generally, and as alternative to the method 100 described above relative to FIG. 3A, to minimize a volume of aqueous two-phase solution being injected, one or more of the bone marrow concentrate or the platelet rich plasma concentrate may be isolated before the extracellular vesicles isolation. Advantageously, in this example, the volume of the extracellular vesicles can be determined, the concentration of aqueous two-phase solution reduced, and the effect of the aqueous two-phase solution upon the cells in the bone marrow concentrate/platelet rich plasma fractions is minimized.

More specifically, another method 200 of isolating vesicles using the system 10 of the present disclosure is described below. Like the method 100 described above, the method 200 includes loading one or more of blood or bone marrow into the input port 12 of the concentration system 10, as indicated in part 1 of FIG. 3A. The method 200 then includes centrifuging one or more of the blood or bone marrow to separate one or more of red blood cells, platelet poor plasma, or platelet rich plasma/bone marrow concentrate fractions via the centrifuge device 14 of the concentration system 10, as indicated in part 2, for a first centrifugation. Unlike the method 100, the method 200 then includes pumping only the bone marrow/platelet rich plasma fractions into a syringe, such as the isolation syringe 26 disposed adjacent to the top portion 25 of the compartment 11, as indicated in part 3 of FIG. 3A. One of ordinary skill in the art will appreciate that only the bone marrow/platelet rich plasma fractions created after the first centrifugation may alternatively be pumped into another syringe or a receptacle different from the isolation syringe 26, for example, and still fall within the scope of the present disclosure. In addition, the method 200 then includes pumping only the platelet poor plasma fractions into the first receptacle 16 of the concentration system 10, as indicated in part 4. In some examples, the method 200 may also further comprises pumping the red blood cells fractions into the second receptacle 18, as indicated in part 5.

Still referring to FIG. 3B, the method 200 also includes adding a concentrated aqueous two-phase solution to the platelet poor plasma fractions disposed within the first receptacle 16, as indicated in part 6, and then drawing the concentrated aqueous two-phase solution and the platelet poor plasma fractions back into the centrifuge device 14 to isolate one or more of extracellular vesicles, as indicated in part 7, for example. In one example, drawing the concentrated aqueous two-phase solution and the platelet poor plasma fractions back into the centrifuge device 14 for a second centrifugation comprises isolating extracellular vesicles from the platelet poor plasma fractions, creating an extracellular vesicles pellet for injection, as explained more below.

Next, the method 200 (like the method 100) may also include pumping the aqueous two-phase solution and extracellular vesicles-poor plasma into the first receptacle 16 after drawing the concentrated aqueous two-phase solution and one or more of the bone marrow concentrate/platelet rich plasma fractions or platelet poor plasma fractions back into the centrifuge device for centrifugation, as indicated in part 8.

In addition, the method 200 also includes pumping only the isolated extracellular vesicles into the syringe 26 disposed adjacent to the top portion 25 of the compartment 11 for injection, as indicated in part 9 of FIG. 3B. More specifically, the extracellular vesicles created from the centrifugation of the concentrated aqueous two-phase solution and the platelet poor plasma fractions drawn back into the centrifuge device 14, for example, e.g., the second centrifugation, may be pumped into a syringe that was filled with the bone marrow concentrate/platelet rich plasma in the first centrifugation. In one example, this syringe may be the isolation syringe 26 disposed adjacent to the top portion 25 of the compartment 11, as depicted in FIGS. 3A and 3B. Thus, in this example, the concentrated aqueous two-phase solution is only added with the extracellular vesicles, greatly reducing any residual concentrated aqueous two-phase in the isolation syringe 26.

As an example, 1 mL of extracellular vesicles may be added to 4 mL of bone marrow concentrate already disposed in the isolation syringe 36 (to be injected, for example), reducing the residual concentrated aqueous two-phase solution, such as PEG-DEX solution, 5-fold. As such, by adding the concentrated aqueous two-phase solution, such as the PEG-DEX solution, to only the platelet poor plasma (as in part 6 of FIG. 3B), and then adding the extracellular vesicles created in the second centrifugation, e.g., platelet poor plasma-extracellular vesicles, to the bone marrow concentrate/platelet rich plasma fractions pumped into the syringe 26 (as in part 3 of FIG. 3B), the residual concentrated aqueous two-phase is reduced. Moreover, as the extracellular vesicles, e.g., platelet poor plasma-extracellular vesicles, are added to the isolation syringe 26, the additional extracellular vesicles volume can be easily determined.

In another example, the method 200 may further comprise determining a volume of PEG-DEX solution to be injected based upon the volume of the bone marrow/platelet rich plasma fractions isolated in the syringe 26. As a result, the concentration of aqueous two-phase solution used is reduced, minimizing the effect of the aqueous two-phase solution on nucleated cells in the bone marrow/platelet rich plasma fractions, for example.

Figure 4:
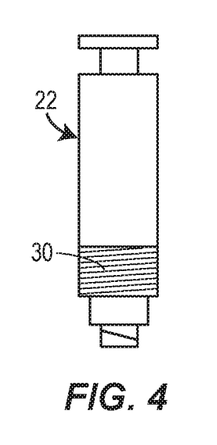
FIG. 4 is a perspective view of a syringe adapted to be used with the system of FIG. 1.
Figure 5:
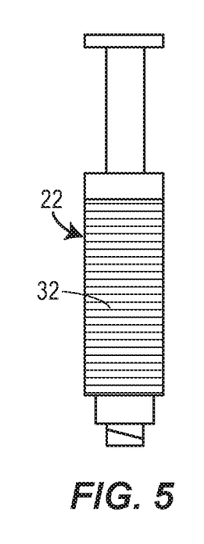
FIG. 5 is a perspective view of the syringe of FIG. 4 with platelet poor plasma added to the syringe.
Figure 6:
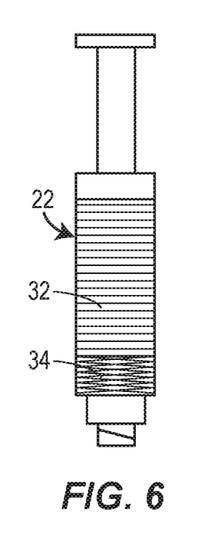
FIG. 6 is perspective view of the syringe of FIG. 4 with an extracellular vesicles pellet created after centrifugation in a centrifuge device of the system of FIG. 1.

Referring now to FIGS. 4-6, a perspective view of a syringe adapted to be used with the system 10 described above is depicted. More specifically, and in one example, the syringe of FIGS. 4-6 may be the syringe 22 depicted in FIG. 2, which is coupled to the first receptacle 16, as described above. In this example, a concentrated aqueous two-phase aqueous two-phase solution is first disposed in the syringe 22, as depicted in FIG. 4. In addition, and as described above relative to method 200, for example, the platelet poor plasma (PPP) is added to the syringe 22 having the aqueous two-phase solution, creating an aqueous two-phase solution, such as a PEG-DEX solution, and PPP solution 32 within the syringe 22, as depicted in FIG. 5. More specifically, and in one example, to get a final 1.5% PEG-DEX concentration, if 1 mL of 15% PEG-DEX is in the syringe 22, 9 mL of platelet poor plasma is drawn into the syringe 22 for a total volume of 10 mL. More generally, an amount of platelet poor plasma may be added to the concentrated aqueous two-phase solution, such as drawn into the syringe 22, such that the amount of the concentrated aqueous two-phase PEG-DEX solution is diluted to a working solution of about 1.5% concentrated aqueous two-phase solution. In addition, and in another example, concentrated aqueous two-phase is added to the platelet poor plasma and allowed about five minutes of room temperature incubation, as described more below.

As depicted in FIG. 6, the aqueous two-phase solution and PPP solution 32 within the syringe 22 is centrifuged in a centrifuge device, creating a pellet 34 of extracellular vesicles for injection or addition to one or more of platelet rich plasma or bone marrow concentrate for example. More specifically, and in one example, the syringe 22 with the aqueous two-phase and PPP solution is centrifuged within a centrifuge device able to hold the syringe 22 for a period of about 10 minutes at 200×g, resulting in the isolation of the extracellular vesicles and creation of the extracellular vesicles pellet 34.

More generally, another method 300 of isolating extracellular vesicles using the system 10 and the syringe 22 depicted in FIGS. 4-6, for example, includes disposing a concentrated aqueous two-phase solution in one or more of a syringe, such as the syringe 22, or a receptacle of the system 10. The method 300 further includes adding one or more of platelet poor plasma fractions or bone marrow/platelet rich plasma fractions into the concentrated aqueous two-phase solution, as depicted in the syringe 22 of FIG. 5, for example. The method 300 also includes centrifuging the solution and one or more of the platelet poor plasma fractions or the bone marrow/platelet rich plasma fractions disposed in the syringe 22 to isolate the extracellular vesicles. As depicted in FIG. 6, the method 300 still further includes creating a pellet 34 having the isolated extracellular vesicles, the pellet 34 for injection. In another example, the extracellular vesicles pellet 34 may be added to one or more of the bone marrow/platelet rich plasma fractions, for example.

Figure 7:
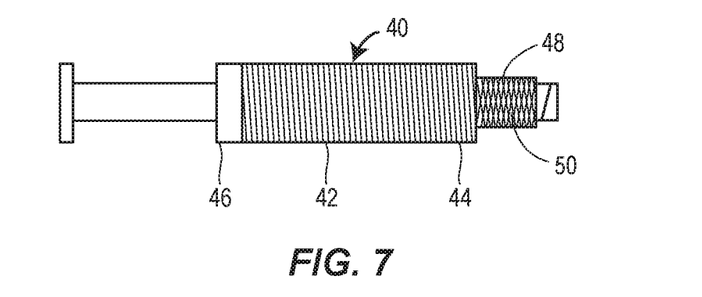
FIG. 7 is a perspective view of another syringe adapted to be used with the system of FIG. 1, the syringe including another exemplary extracellular vesicles pellet.
Figure 8:
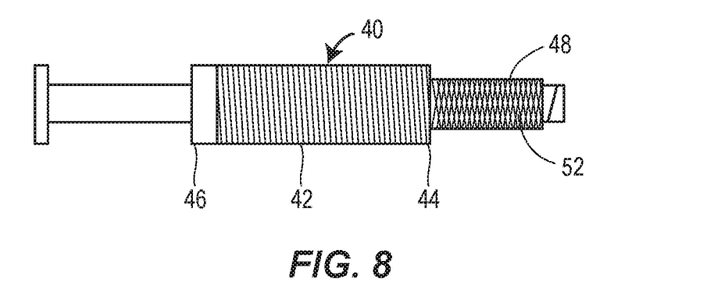
FIG. 8 is a perspective view of a syringe adapted to be used with the system of FIG. 1, the syringe including another exemplary extracellular vesicles pellet and one or more of bone marrow concentrate fractions or platelet rich plasma fractions.

As depicted in FIGS. 7 and 8, an alternative syringe 40 may be designed to accommodate one or both of only the extracellular vesicles pellet, as depicted in FIG. 7, or the combination of the extracellular vesicles pellet and the bone marrow concentrate or platelet rich plasma, as depicted in FIG. 8. More specifically, and referring now to FIG. 7, the syringe 40 may include a body 42 having a distal end 44 and a proximal end 46. A projection 48, such as a cylindrical projection, extends from the distal end 44 of the body 42 and includes the extracellular vesicles pellet 50 formed by the centrifuging process described above. In this example, and unlike the syringe 22 of FIGS. 4-6, the syringe 40 of FIGS. 7 and 8 receives the extracellular vesicles pellet 50 in the projection 48 disposed outside of the body 42 of the syringe 40 and not within the body 42, as depicted in FIGS. 4-6, for example. Likewise, FIG. 8 depicts the projection 48 of the syringe 40 having a pellet 52 including both the extracellular vesicles and one or more of the bone marrow concentrate or platelet rich plasma. By having the extracellular pellets 50, 52 disposed in the projection 48 of the syringe 40 and not the main body 42, the extracellular vesicles concentrate can be more easily expelled from the syringe 40 while minimizing the volume of the extracellular vesicles-poor plasma and the aqueous two-phase solution, such as PEG-DEX, that is expelled from the syringe 40, for example.

All of the methods 100, 200, 300 described above may further include premixing the PEG-DEX solution at a predetermined concentration before adding the concentrated aqueous two-phase solution to one or more of the bone marrow concentrate/platelet rich plasma fractions and platelet poor plasma fractions. In one example, premixing the PEG-DEX solution at a predetermined concentration includes premixing the PEG-DEX solution at a 10× concentration. In another example, premixing the PEG-DEX solution at a predetermined concentration includes premixing the PEG-DEX solution at a 5× concentration. In yet another example, premixing the PEG-DEX solution at a predetermined concentration includes premixing the PEG-DEX solution at an 8× concentration. In other examples, and as one of ordinary skill in the art will understand, the predetermined concentration may be any concentration within the range of 3× concentration to 15× concentration and still fall within the scope of the present disclosure. In some examples, premixing the PEG-DEX solution is essential for quick extracellular vesicles isolation. In addition, the methods 100, 200, 300 may include allowing a period of time for room temperature incubation after adding the concentrated aqueous two-phase solution to one or more of the bone marrow concentrate/platelet rich plasma fractions and platelet poor plasma fractions. In one example, the period of time for room temperature incubation is about five minutes. One of ordinary skill in the art will appreciate that the period of time may be more or slightly less than five minutes, such as three, four or four in a half minutes, and still fall within the scope of the present disclosure.

In addition, in each of the methods 100, 200, 300, adding a concentrated aqueous two-phase solution to one or more of the bone marrow concentrate/platelet rich plasma fractions and platelet poor plasma fractions may comprise adding the concentrated aqueous two-phase solution to one or more of the bone marrow concentrate/platelet rich plasma fractions and platelet poor plasma fractions based upon a volume of one or more of the bone marrow concentrate/platelet rich plasma fractions and platelet poor plasma fractions in the first receptacle 16.

Figure 9:
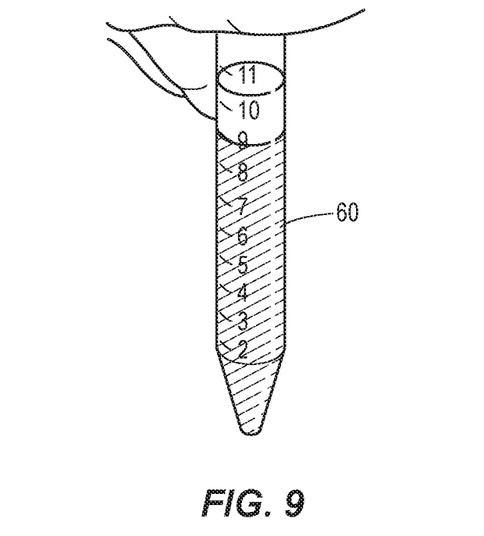
FIG. 9 is a perspective view of a receptacle adapted to be coupled to the system of FIG. 1.

Referring now to FIGS. 9-12, various experimental results of the system 10 and methods 100, 200, and 300 of the present disclosure are depicted. More specifically, FIG. 9 is a perspective view of an aqueous two-phase solution and platelet poor plasma combination in a receptacle 60 before centrifugation. As indicated therein, before centrifugation no extracellular vesicles have been isolated. In this example, the aqueous two-phase solution is PEG-DEX. In addition, a 1.5% PEG-DEX concentration when added to the platelet poor plasma enabled the extracellular vesicles isolation with a tabletop centrifuge, such as a centrifuge device able to hold the syringe, for example. In addition, 450 k-650 k molecular weight dextran was employed and the centrifuge device was run for 10 minutes at 1000×g. As will be appreciated, various other percentage amounts of PEG-DEX concentration and, more generally, a first phase of the aqueous two-phase solution may alternatively be used and still fall within the scope of the present disclosure. Likewise, various other weights of dextran and, more generally, a second phase of the aqueous two-phase solution, may also be used and still fall within the scope of the present disclosure. Said another way, various combinations of PEG-DEX solution may be added to the platelet poor plasma to enable extracellular vesicle isolation during centrifugation. More generally, various combinations of the first phase of the aqueous two-phase solution and the second phase of the aqueous two-phase solution may be used to enable the extracellular vesicle isolation during centrifugation and still fall within the scope of the present disclosure.

Figure 10:
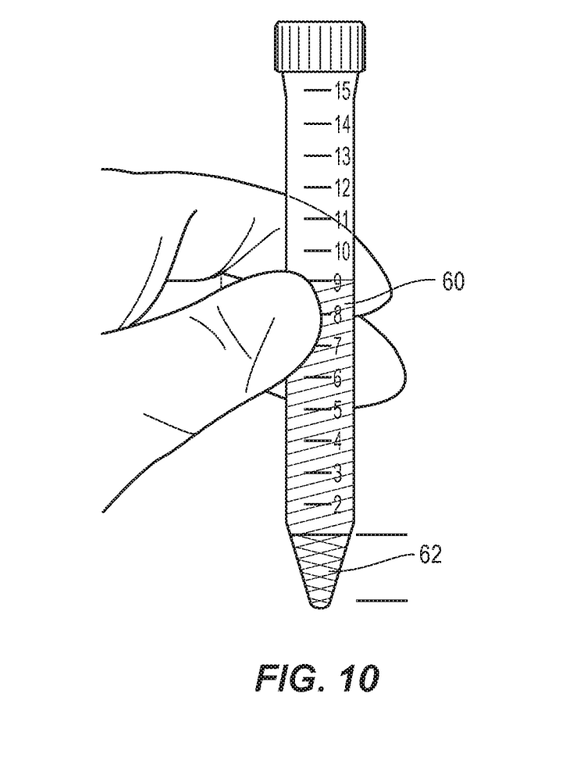
FIG. 10 is a perspective view of the receptacle of FIG. 9 after a ten minute centrifugation process, the receptacle having an extracellular vesicles pellet.

Referring now to FIG. 10, a perspective view of the receptacle 60 of FIG. 9 after a 10 minute centrifugation process, for example, is depicted. The process and the foregoing experimental parameters noted resulted in the isolation of extracellular vesicles, and the creation of the extracellular vesicles pellet 62.

Figure 11:
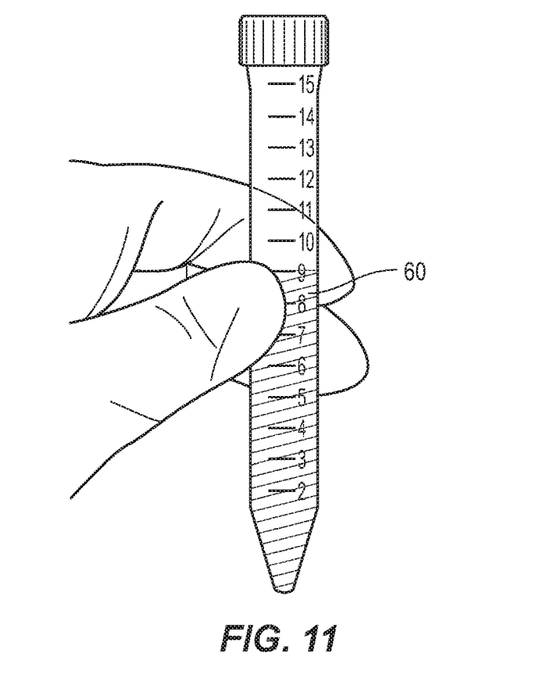
FIG. 11 is a perspective view of a receptacle adapted to be coupled to the system of FIG. 1.

Referring now to FIG. 11, the receptacle 60 is depicted with a PEG-DEX concentration and ddH$_2$O combination disposed therein. Centrifugation was conducted, and no creation of extracellular vesicle pellets resulted.

Figure 12:
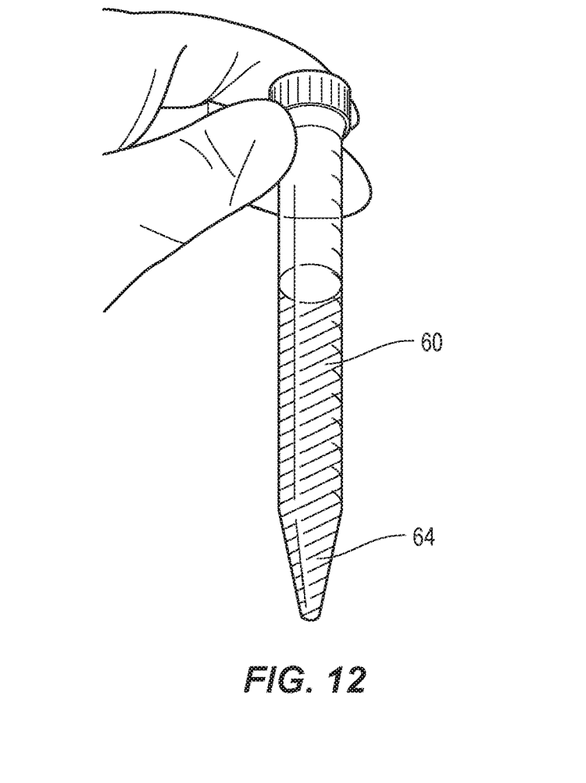
FIG. 12 is a perspective view of the receptacle of FIG. 9, the platelet poor plasma was prespun to completely remove residual cells.

Referring now to FIG. 12, the receptacle 60 is depicted after centrifugation. In this experimental example, a PEG-DEX concentrate solution and platelet poor plasma combination was again disposed within the receptacle 60 before centrifugation. Before disposing the platelet poor plasma with the PEG-DEX concentrate solution, the platelet poor plasma was prespun for 30 minutes at 1900×g to completely remove any residual cells, for example. After centrifugation, an extracellular vesicles pellet 64 was still created and recovered, as depicted in FIG. 12.

Figure 13:
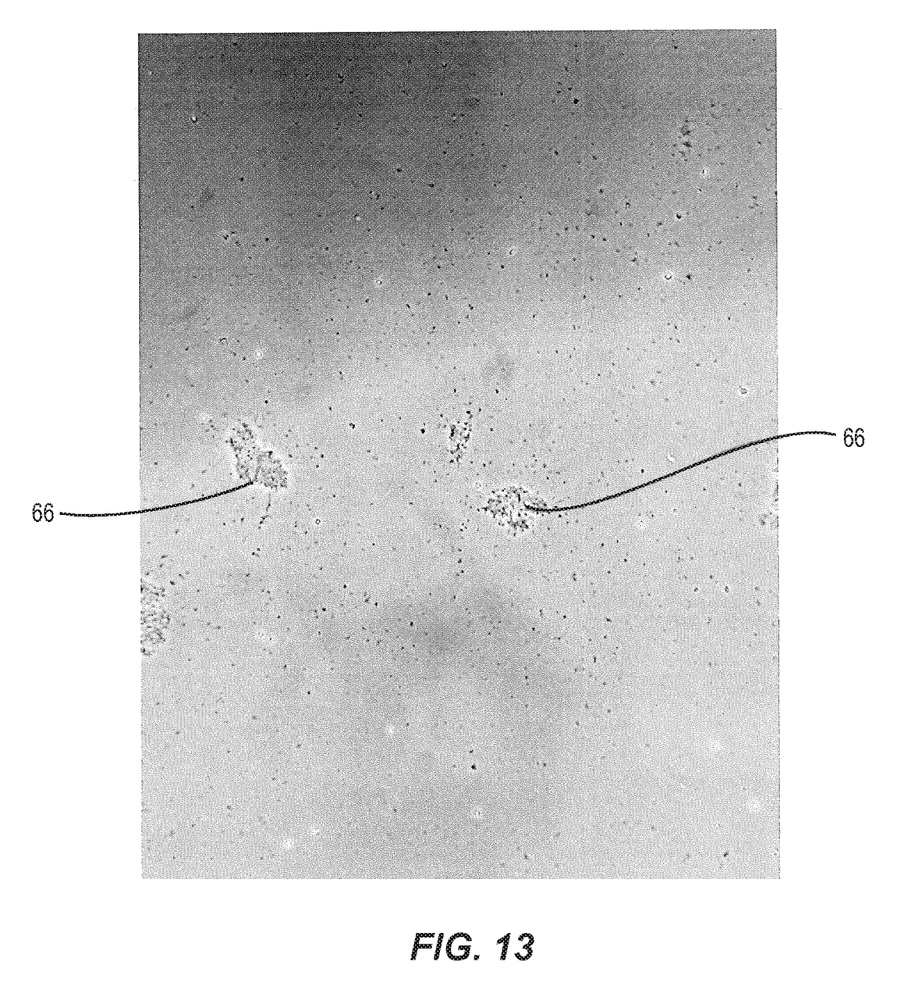
FIG. 13 is a phase-contrast photograph, depicting an extracellular vesicles pellet resuspended at a 20× magnification.

Referring now to FIG. 13, a phase-contrast photograph of an exemplary extracellular vesicles pellet is depicted. Specifically, the extracellular vesicles pellet is resuspended at 20× magnification. No cells are depicted in this view, but extracellular vesicle clusters 66 can be seen.

In view of the foregoing, one of ordinary skill in the art will appreciate the following advantages of the system 10 and methods 100, 200, 300 of the present disclosure described above. For example, the system 10 and methods 100, 200, 300 can isolate extracellular vesicles from platelet poor plasma quickly and in a clinical setting. By isolating the extracellular vesicles quickly, the extracellular vesicles can be applied within the same clinical procedure that included the collection of one or more of blood or bone marrow, which is important for practical, therapeutic, and regulatory reasons. For example, the extracellular vesicles isolated from blood or bone marrow can be employed to enhance the efficacy of biological injections, or as a stand-alone biological therapeutic.

In addition, the system 10 enables the collection of extracellular vesicles from the platelet poor plasma fraction, which is typically unused, but is a substantial portion of the output of the centrifugation process by volume in conventional systems. Moreover, the syringes 22, 26, 40, for example, of the system 10 may be designed such that the syringe 22, 26, 40 may be loaded into the centrifuge device 14 so no transfer of platelet poor plasma and the aqueous two-phase solution, such as the PEG-DEX solution, or the extracellular vesicles concentrate to a centrifuge tube is necessary. So configured, the risk of contamination is minimized, the risk for error or sample loss is reduced, and the procedure is faster.

Moreover, the system 10 is designed such that only one centrifuge device 14 is used, even though the biological sample is run through two centrifugation cycles, as explained more above. As a result, the need for an additional centrifugation device and additional centrifuge syringes is eliminated. In addition, the risk of contamination is further reduced, and the isolation procedure is faster.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Some implementations may be described using the expression "coupled" along with its derivatives. For example, some implementations may be described using the term "coupled" to indicate that two or more elements are in direct physical or electrical contact. The term "coupled," however, may also mean that two or more elements are not in direct contact with each other, but yet still co-operate or interact with each other. The implementations are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the implementations herein. This is done merely for convenience and to give a general sense of the invention. This description should be read to include one or at least one and the singular also includes the plural unless it is obvious that it is meant otherwise.

Further, while particular implementations and applications have been illustrated and described, it is to be understood that the disclosed implementations are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A method of isolating extracellular vesicles or platelet rich plasma fractions, the method comprising:
   loading one or more of blood or bone marrow into an input port of a concentration system;
   centrifuging one or more of the blood or bone marrow to separate one or more of red blood cells, platelet poor plasma fractions, or platelet rich plasma fractions via a centrifuge device of the concentration system;
   collecting one or more of: (1) platelet rich plasma fractions; and (2) platelet poor plasma fractions into a first receptacle of the concentration system;
   adding a concentrated aqueous two-phase solution to one or more of the: (1) platelet rich plasma fractions; and (2) platelet poor plasma fractions;
   drawing the concentrated aqueous two-phase solution and one or more of the: (1) platelet rich plasma fractions; or (2) platelet poor plasma fractions back into the centrifuge device; and
   isolating one or more of: (1) extracellular vesicles from the platelet poor plasma fractions; and (2) extracellular vesicles and platelet rich plasma fractions from the platelet rich plasma fractions, wherein drawing the concentrated aqueous two-phase solution and one or more of the: (1) platelet rich plasma fractions; or (2) platelet poor plasma fractions back into the centrifuge device for centrifugation comprises centrifuging the aqueous two-phase solution and the platelet poor plasma fractions and the isolating the extracellular vesicles from the platelet poor plasma fractions, and creating a pellet for injection, the pellet comprising the extracellular vesicles.

2. The method of claim 1, wherein adding a concentrated aqueous two-phase solution to one or more of the: (1) platelet rich plasma fractions; and (2) platelet poor plasma fractions comprises adding a concentrated polyethylene glycol-dextran (PEG-DEX) solution to one or more of the: (1) platelet rich plasma fractions; and (2) platelet poor plasma fractions, the method further comprising premixing the concentrated aqueous two-phase solution at a predetermined concentration before adding the concentrated aqueous two-phase solution to one or more of the: (1) platelet rich plasma fractions; and (2) platelet poor plasma fractions.

3. The method of claim 2, further comprising incubating at room temperature the aqueous two phase solution and the one or more of the (1) platelet rich plasma fractions; or (2) platelet poor plasma fractions for a period of time after adding the concentrated aqueous two-phase solution to one or more of the: (1) platelet rich plasma fractions or bone marrow fractions; and (2) platelet poor plasma fractions.

4. The method of claim 1, further comprising collecting the concentrated aqueous two-phase solution and an extracellular vesicles-poor plasma into the first receptacle after drawing the concentrated aqueous two-phase solution and one or more of the platelet rich plasma fractions or platelet poor plasma fractions back into the centrifuge device for centrifugation.

5. The method of claim 1, wherein adding a concentrated aqueous two-phase solution to one or more of the: (1) platelet rich plasma fractions; and (2) platelet poor plasma fractions comprises adding the concentrated aqueous two-phase solution to one or more of the: (1) platelet rich plasma fractions; and (2) platelet poor plasma fractions based upon a volume of one or more of the: (1) platelet rich plasma fractions; and (2) platelet poor plasma fractions in the first receptacle.

6. The method of claim 1, wherein collecting one or more of: (1) platelet rich plasma fractions: and (2) platelet poor plasma fractions in a first receptacle of the concentration system comprises collecting only the platelet poor plasma fractions in the first receptacle and then pumping the platelet rich plasma fractions into a syringe.

7. The method of claim 6, wherein adding a concentrated aqueous two-phase solution to one or more of: (1) platelet rich plasma fractions; and (2) platelet poor plasma fractions comprises adding a concentrated aqueous two-phase solution to only the platelet poor plasma fractions.

8. The method of claim 7, wherein drawing the concentrated aqueous two-phase solution and one or more of the platelet rich plasma fractions or platelet poor plasma fractions back into the centrifuge device for centrifugation comprises drawing the concentrated aqueous two-phase solution and the platelet poor plasma fractions back into the centrifuge device for centrifugation and centrifuging the concentrated aqueous two-phase solution and the platelet poor plasma fractions.

9. The method of claim 6, further comprising determining a volume of aqueous two-phase solution to be added based upon a volume of the platelet rich plasma fractions isolated pumped into the syringe, reducing the concentration of aqueous two-phase solution used and minimizing the effect of the aqueous two-phase solution on nucleated cells in the platelet rich plasma fractions.

10. The method of claim 9, further comprising determining a volume of the extracellular vesicles based on the volume of the platelet rich plasma fractions pumped into the syringe.

11. The method of claim 1, further comprising pumping platelet rich plasma fractions into a syringe for injection after centrifuging one or more of the blood or bone marrow to separate one or more of red blood cells, platelet poor plasma fractions, or platelet rich plasma fractions via a centrifuge device of the concentration system.

12. The method of claim 11, wherein adding the concentrated aqueous two-phase solution to only the platelet poor plasma fractions, and then pumping the extracellular vesicles into the syringe for injection, the syringe including the platelet rich plasma fractions, results in diluting residual concentrated aqueous two-phase solution in the syringe.

13. A method comprising: disposing a concentrated aqueous two-phase solution in a syringe or a receptacle; adding one or more of (1) platelet poor plasma fractions or (2) platelet rich plasma fractions into the concentrated aqueous two-phase solution; centrifuging the concentrated aqueous two-phase solution and one or more of the (1) platelet poor plasma fractions or the platelet rich plasma fractions disposed in the syringe or the receptacle and isolating one or more of extracellular vesicles and platelet rich plasma fractions or; and preparing one or more of (1) extracellular vesicles or (2) platelet rich plasma fractions from the centrifuging of the concentrated aqueous two-phase solution and one or more of the platelet poor plasma fractions and the platelet rich plasma fractions such that the fractions are suitable for injection.

14. The method of claim 13, wherein disposing a concentrated aqueous two-phase solution in a syringe or a receptacle comprises disposing a concentrated PEG-DEX solution in a syringe or a receptacle.

15. The method of claim 13, wherein adding one or more of platelet poor plasma fractions or platelet rich plasma fractions into the concentrated aqueous two-phase solution comprises adding an amount of platelet poor plasma fractions such that the amount of the concentrated aqueous two-phase solution is diluted.

16. The method of claim 13, further comprising incubating one or more of the platelet poor plasma fractions or the platelet rich plasma fractions and the concentrated aqueous two-phase solution at room temperature for a period of time after adding one or more of platelet poor plasma fractions or platelet rich plasma fractions into the concentrated aqueous two-phase solution.

17. The method of claim 13, further comprising mixing the extracellular vesicle with a biofluid, the biofluid including one or more of (1) platelet rich plasma fractions; (2) bone marrow concentrate; or (3) platelet poor plasma fractions.

18. A method comprising: adding one or more of platelet poor plasma fractions or platelet rich plasma fractions to a concentrated aqueous two-phase solution; centrifuging the concentrated aqueous two-phase solution and one or more of the platelet poor plasma fractions or platelet rich plasma fractions to isolate one or more of extracellular vesicles or platelet rich plasma fractions; and preparing for injection one or more of extracellular vesicles or platelet rich plasma fractions from the centrifuging of the concentrated aqueous two-phase solution and one or more of the platelet poor plasma fractions the platelet rich plasma fractions.

19. The method of claim 18, wherein preparing for injection one or more of extracellular vesicles platelet rich plasma fractions from centrifuging of the concentrated aqueous two-phase solution and one or more of the platelet poor plasma fractions or platelet rich plasma fractions comprises preparing for injection extracellular vesicles from centrifuging the concentrated aqueous two-phase solution and one or more of the platelet poor plasma fractions and the platelet rich plasma fractions.

20. The method of claim 18, further comprising incubating one or more of the platelet poor plasma fractions or the platelet rich plasma fractions and the concentrated aqueous two-phase solution at room temperature for a period of time after adding a concentrated aqueous two-phase solution to one or more of: (1) platelet poor plasma fractions; or (2) platelet rich plasma fractions.

21. The method of claim 18, further comprising mixing the extracellular vesicles with a biofluid, the biofluid including one or more of platelet rich plasma, bone marrow concentrate, or platelet poor plasma fractions.

22. The method of claim 18, wherein disposing a concentrated aqueous two-phase solution in a syringe or a receptacle comprises disposing a concentrated PEG-DEX solution in a syringe or a receptacle.

* * * * *

UNITED STATES PATENT AND TRADEMARK OFFICE
CERTIFICATE OF CORRECTION

PATENT NO. : 11,660,271 B2
APPLICATION NO. : 16/259648
DATED : May 30, 2023
INVENTOR(S) : Mark Katakowski et al.

It is certified that error appears in the above-identified patent and that said Letters Patent is hereby corrected as shown below:

In the Claims

At Column 14, Line 19, "two phase" should be -- two-phase --.

At Column 14, Line 42, "fractions:" should be -- fractions; --.

At Column 14, Lines 63-64, "fractions isolated pumped" should be -- fractions pumped --.

At Column 15, Line 6, "platelet" should be -- the platelet --.

At Column 15, Line 8, "platelet" should be -- the platelet --.

At Column 15, Line 9, "platelet" should be -- the platelet --.

At Column 16, Line 22, "vesicles platelet" should be -- vesicles or platelet --.

Signed and Sealed this
Ninth Day of July, 2024

Katherine Kelly Vidal
*Director of the United States Patent and Trademark Office*